US009752730B2

(12) United States Patent
Voelz

(10) Patent No.: US 9,752,730 B2
(45) Date of Patent: Sep. 5, 2017

(54) METHOD AND DIALYSIS MACHINE INCLUDING CALIBRATION CONTAINER

(71) Applicant: Fresenius Medical Care Holdings, Inc., Waltham, MA (US)

(72) Inventor: Phillip Voelz, Sandpoint, ID (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 558 days.

(21) Appl. No.: 13/679,490

(22) Filed: Nov. 16, 2012

(65) Prior Publication Data

US 2014/0138291 A1 May 22, 2014

(51) Int. Cl.
*B01D 61/30* (2006.01)
*F17D 3/00* (2006.01)
*A61M 1/16* (2006.01)

(52) U.S. Cl.
CPC ............... *F17D 3/00* (2013.01); *A61M 1/16* (2013.01); *A61M 2205/70* (2013.01); *Y10T 137/0402* (2015.04)

(58) Field of Classification Search
CPC ........ A61M 1/16; A61M 2205/70; F17D 3/00
USPC .............. 137/15.01; 210/232, 238, 321.6, 85
See application file for complete search history.

(56) References Cited

U.S. PATENT DOCUMENTS

| 4,439,188 | A | * | 3/1984 | Dennehey et al. ............ 604/534 |
| 5,312,547 | A | * | 5/1994 | Kruger et al. ................. 210/317 |
| 5,643,190 | A | * | 7/1997 | Utterberg ............. A61M 1/3621 604/6.15 |
| 5,697,900 | A | | 12/1997 | Peluso et al. |
| 6,691,047 | B1 | * | 2/2004 | Fredericks .......... A61M 1/3621 128/204.18 |
| 2004/0232061 | A1 | | 11/2004 | Dillon |
| 2008/0200868 | A1 | * | 8/2008 | Alberti ..................... A61M 1/28 604/29 |
| 2009/0187138 | A1 | | 7/2009 | Lundtveit et al. |
| 2009/0204086 | A1 | * | 8/2009 | Kizer ................. A61B 10/0045 604/322 |

* cited by examiner

Primary Examiner — Dirk Bass
(74) Attorney, Agent, or Firm — Leydig, Voit & Mayer, Ltd.

(57) ABSTRACT

A dialysis machine includes an ultrafiltration pump that pumps fluid from a pump inlet to a pump outlet, and a calibration fluid container. The container including a bottom, an upstanding sidewall, a container inlet and a container outlet, the bottom and the upstanding sidewall defining a container interior. The container may be to the atmosphere. At least the container outlet being disposed in the sidewall proximate to the bottom. The first end of a first hose is fluidly coupled to the pump inlet, and the second end of the first hose is removably, fluidly coupleable to the container outlet. The first end of a second hose is fluidly coupled to the pump outlet, and the second end of the second hose is removably, fluidly coupleable to the container inlet. In this way, a calibration process may be performed when the second ends of the first and second hoses are fluidly coupled to the container outlet and the container inlet, respectively.

7 Claims, 6 Drawing Sheets

METHOD AND DIALYSIS MACHINE INCLUDING CALIBRATION CONTAINER

TECHNICAL FIELD

This patent disclosure relates generally to systems for dialysis and, more particularly to the calibration of a dialysis system pump.

BACKGROUND

Dialysis is performed as a treatment for patients suffering from renal insufficiency. Dialysis can be performed either in the peritoneum, or through extracorporeal dialysis or filtration of blood. These two dialysis methods have in common the fact that dialysis fluids or dialysates take up the degradation products of metabolism. These dialysates usually contain high levels of sodium chloride and other electrolytes, such as calcium chloride, or potassium chloride, a buffer substance, such as bicarbonate, or acetate and acid to establish a physiological pH, plus optionally, glucose or another osmotic agent.

Dialysis systems include one or more pumps are used to move fluids utilized during dialysis. It is important that the flow of fluids be monitored and closely controlled. Accordingly, pumps are calibrated on a regular basis to ensure accurate and repeatable flow based upon volume and pressure. During calibration, hoses from either side of the pump are utilized to provide the pump with calibration fluid, generally reverse osmosis, or RO, water. The pump pumps a measured amount of fluid for a period of time. Typically, the hoses are simply placed in an external bucket of RO water; the pump draws RO water in from the bucket through one hose and returns it to the bucket through the other. Upon completion of the calibration, the bucket is emptied. During the calibration process, however, it is not uncommon for the hoses to become dislodged from the bucket. External spillage as the pump returns RO water may result in a dangerous condition, while a dry draw as the pump attempts to draw in RO water may result in an ineffective calibration process.

SUMMARY

The disclosure describes, in one aspect, a dialysis machine having an ultrafiltration pump that has a pump inlet and a pump outlet. The ultrafiltration pump is adapted to pump fluid from the pump inlet to the pump outlet. The machine further includes a calibration fluid container, a first hose, and a second hose. The container includes a bottom, an upstanding sidewall, a container inlet and a container outlet disposed in the sidewall proximate to the bottom. The bottom and the upstanding sidewall define a container interior, the container being open to the atmosphere. The first hose and the second hose each have first and second ends. The first end of the first hose is fluidly coupled to the pump inlet, and the second end of the first hose is removably, fluidly coupleable to the container outlet. The first end of the second hose is fluidly coupled to the pump outlet, and the second end of the second hose being removably, fluidly coupleable to the container inlet. A calibration process may be performed when the second ends of the first and second hoses are fluidly coupled to the container outlet and the container inlet, respectively.

The disclosure describes, in another aspect, a method for calibrating an ultrafiltration pump in a dialysis machine. The ultrafiltration pump has a pump inlet and a pump outlet, and is adapted to pump fluid from the pump inlet to the pump outlet. The dialysis machine has first and second hoses, each of which has first and second ends. The first end of the first hose is fluidly coupled to the pump inlet. The first end of the second hose is fluidly coupled to the pump outlet. The method includes the step of providing a calibration fluid container; the container includes a bottom, an upstanding sidewall, a container inlet and a container outlet; the bottom and the upstanding sidewall define a container interior open to the atmosphere; at least the container outlet is disposed in the sidewall proximate to the bottom. The method further includes the steps of removably, fluidly coupling the second end of the first hose to the container outlet, removably, fluidly coupling the second end of the second hose to the container inlet, and performing a calibration process on the ultrafiltration pump.

BRIEF DESCRIPTION OF THE DRAWING(S)

FIG. 1 is a schematic diagram the general environment where the system is operating. A patient is shown attached to a dialysis apparatus. It is understood that the system of the present invention supplies dialysate solution to such an apparatus for use in hemodialysis.

DETAILED DESCRIPTION

Figure 1:
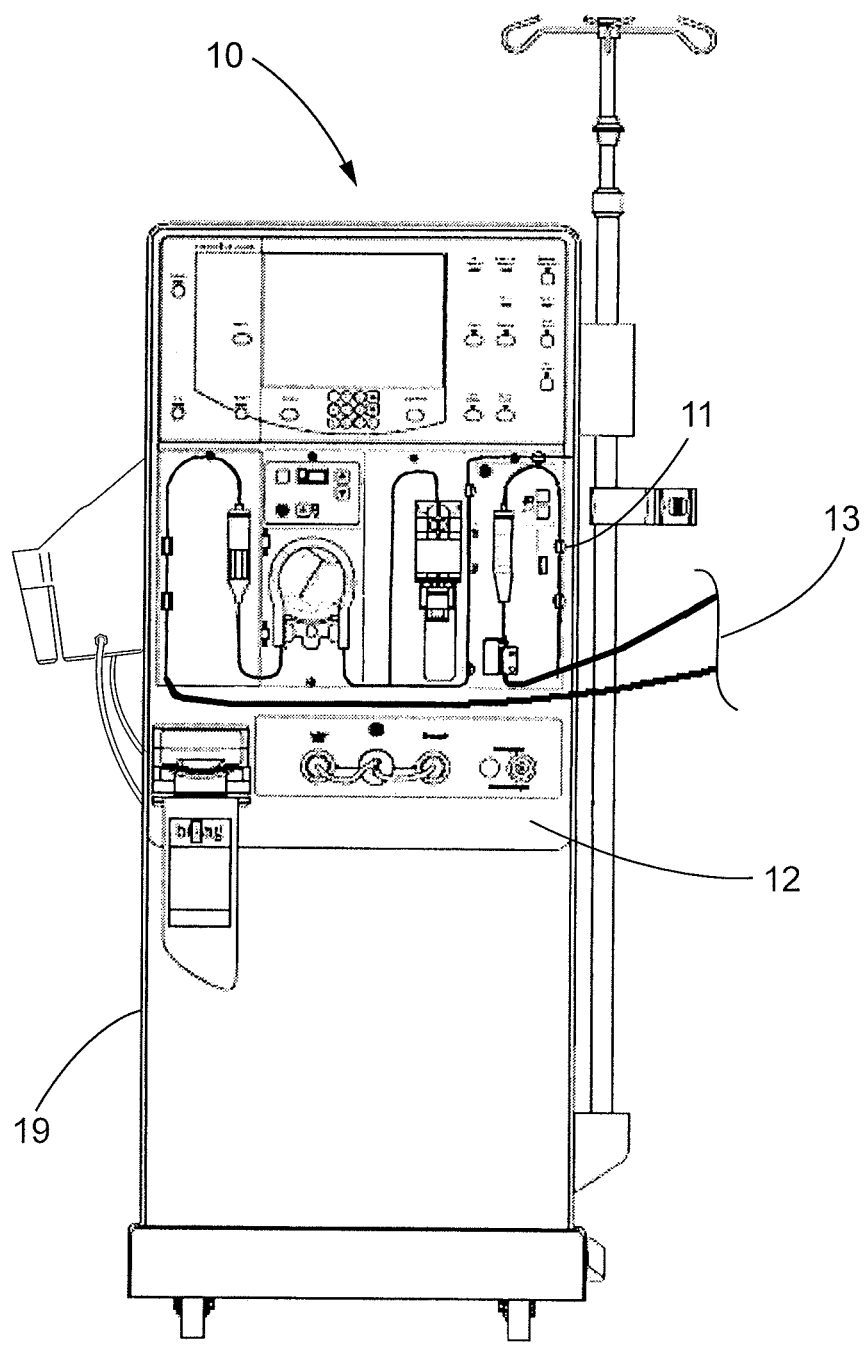
Figure 2:
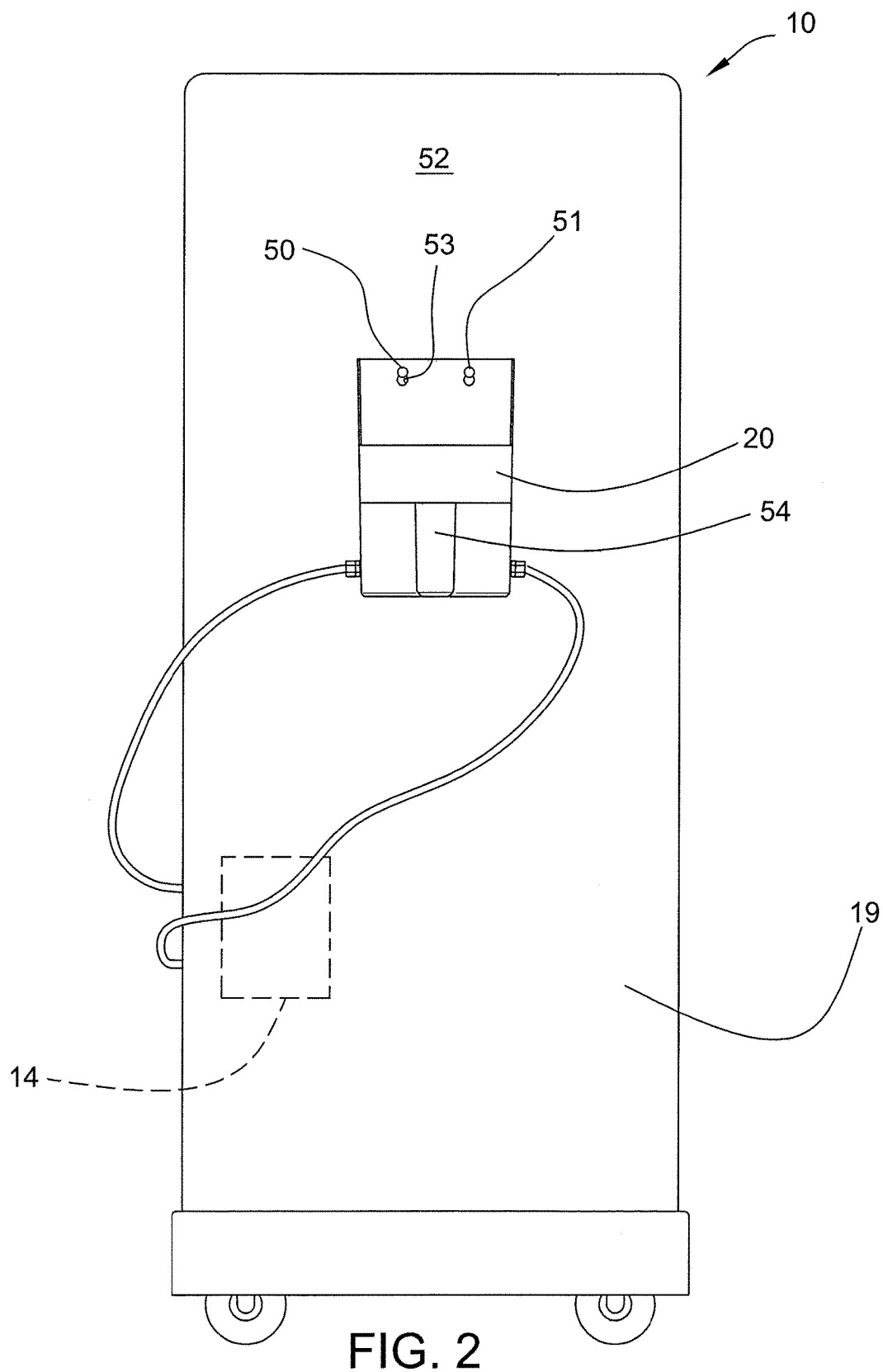
FIG. 2 is a left side elevational view of the dialysis machine of FIG. 1 with a calibration fluid container attached in accordance with the disclosure.
Figure 3:
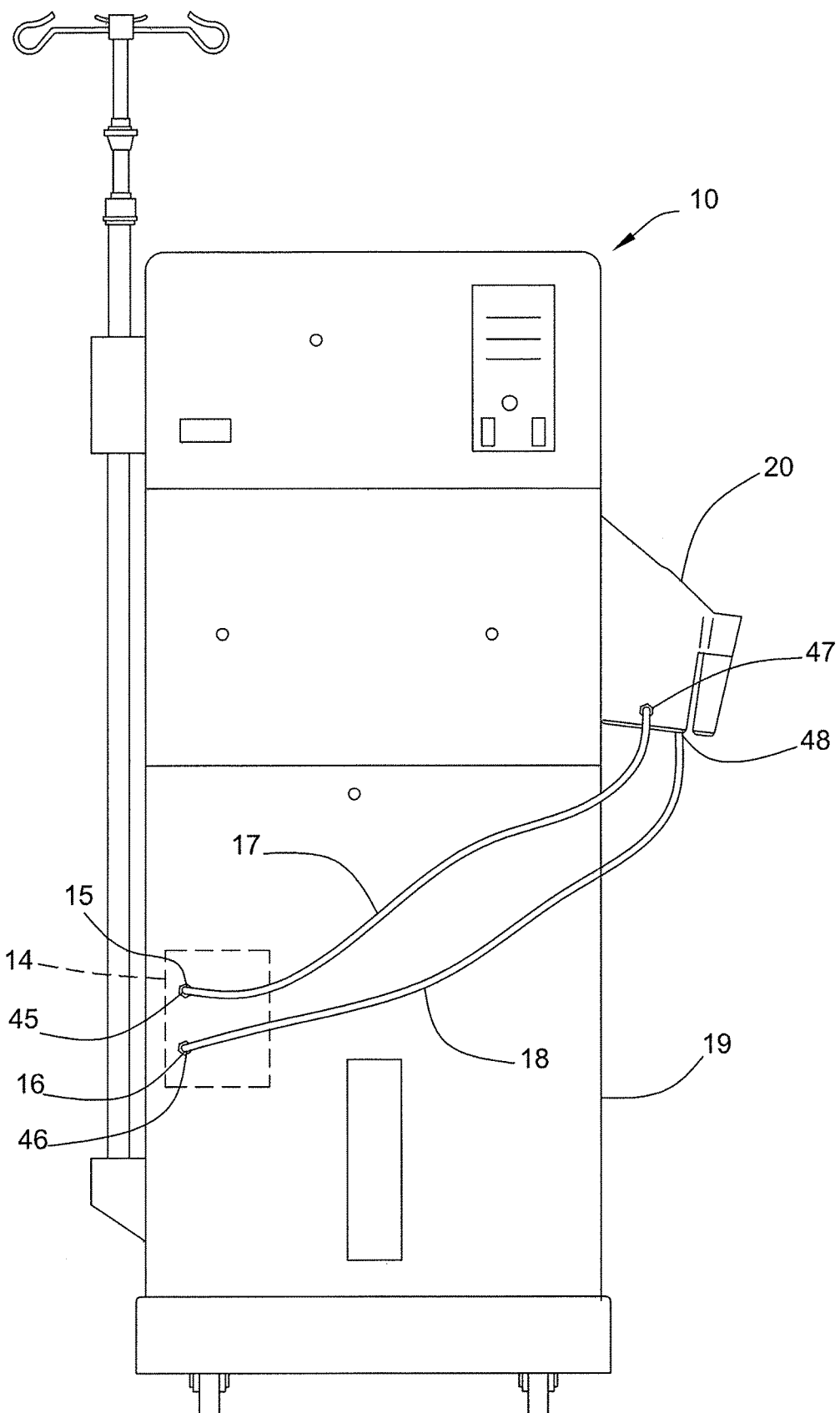
FIG. 3 is a rear elevational view of the dialysis machine of FIG. 1 with a calibration fluid container attached in accordance with the disclosure.
Figure 4:
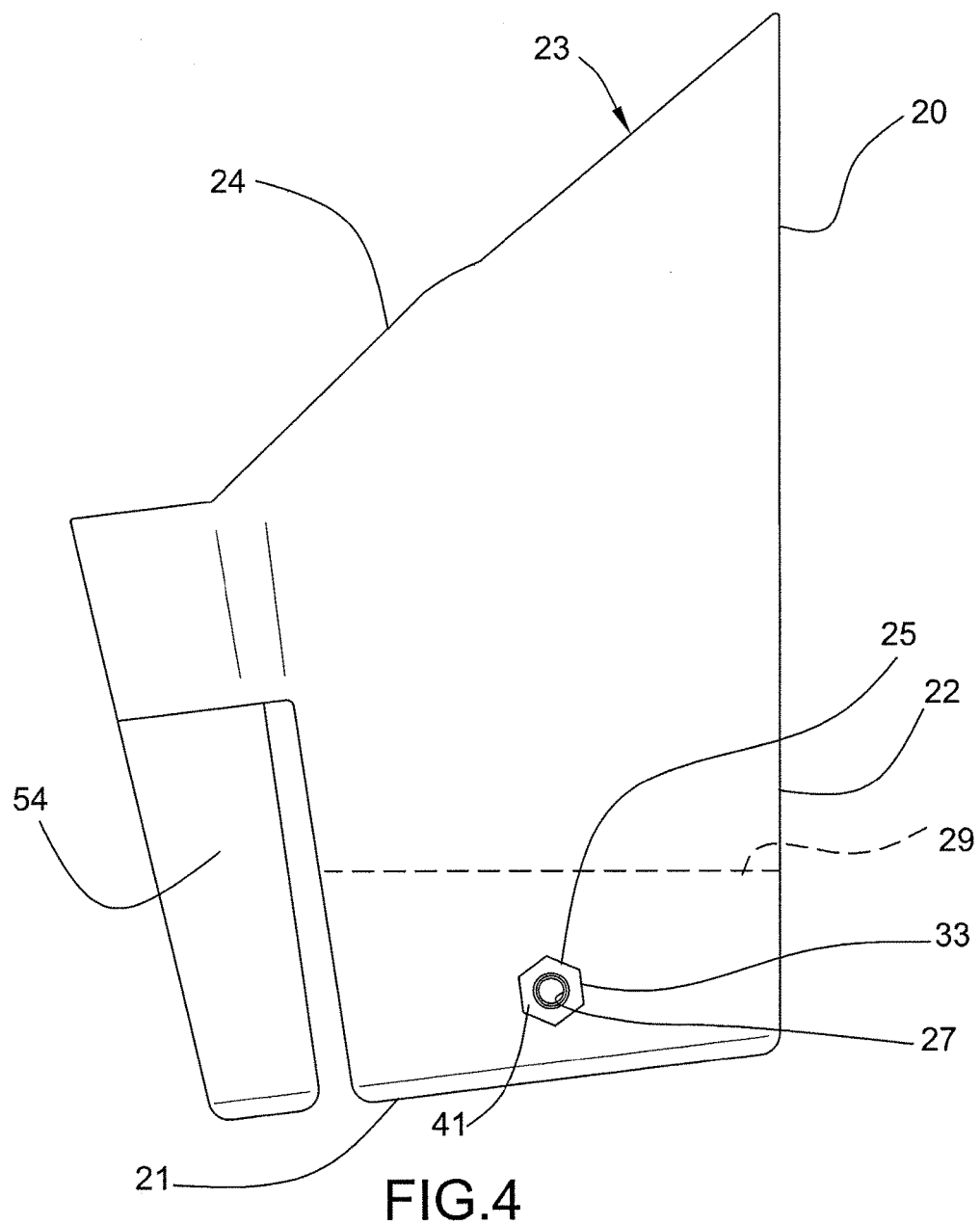
FIG. 4 is a right side elevational view of the calibration fluid container of FIGS. 2 and 3.
Figure 5:
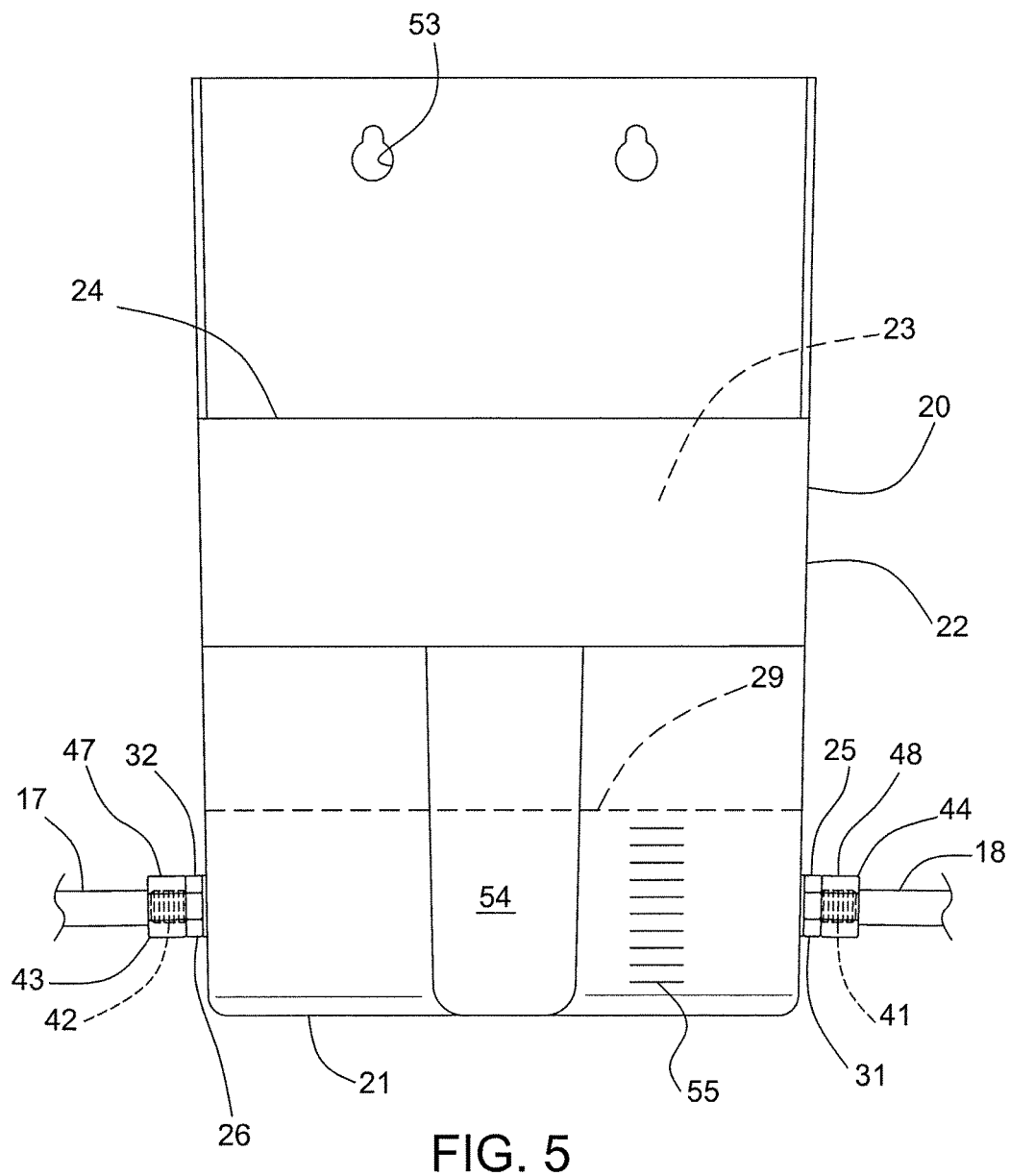
FIG. 5 is a front elevational view of the calibration fluid container of FIGS. 2-4.

Turning now to the drawings, FIG. 1 displays the general context of a dialysis machine 10. The dialysis machine 10 includes the dialyzer 11, and a subsystem 12 for preparing a salt solution from a powdered salt concentrate for use in the dialyzer 11. Alternately, the solution be provided in a prepared form. The solution is provided to the dialyzer 11 for administration to a patient (who would be located in the area generally identified at 13). The dialysis machine 10 may additionally include various other optional subsystems and equipment.

Referring to FIGS. 2-5, the dialysis machine 10 includes an ultrafiltration pump 14 (shown schematically in FIGS. 2 and 3) disposed to advance dialysate through the dialysis machine 10. The ultrafiltration pump 14 may be of any appropriate type, such as, by way of example only, a peristaltic pump, a diaphragm pump, etc. Moreover, the ultrafiltration pump may be operated by appropriate mechanism, such as, by way of example only, a screw mechanism, a stepper motor, fluid activation, etc. The ultrafiltration pump 14 pumps dialysate from a pump inlet 15 to a pump outlet 16. First and second hoses 17, 18 are fluidly coupled to the pump inlet 15 and the pump outlet 16, respectively. In this way, fluid flows through the first hose 17 to the pump inlet 15, through the ultrafiltration pump 14, and out of the pump outlet 16 to the second hose 18. It will be appreciated by those of skill in the art that the hoses 16, 18 may be integrated with one or more parts of the pump. For example, with a peristaltic pump, the first and second hoses 17, 18 may be a single hose that extends through the peristaltic pump. In an arrangement with a single hose extending through the peristaltic pump, the inlet and the outlet of the pump are likewise integrated with the single hose. That is, the inlet of the pump is disposed substantially at that position along the hose where the hose is first compressed by the pump to provide a pillow of fluid, and the outlet is disposed substantially at that position along the hose where the pump releases compression on the hose to allow the fluid to continue to advance through the second hose 18. It will also be appreciated by those of skill in the art that the illustrated embodiment is schematic, and that the hoses 17, 18 may be coupled to the pump inlet and outlet 15, 16 by fittings along a housing 19 of the dialysis machine 10, and/or further hose couplings (not shown). In any event, however, the hoses 17, 18 are fluidly coupled to the pump inlet and outlet 15, 16, be it directly or by way of fittings or further hoses.

The dialysis machine 10 further includes a calibration fluid container 20. While the container 20 is illustrated mounted on the machine 10, it will be appreciated that calibration utilizing the container 20 may be performed with the container 20 at a higher or lower level, such as seated on the floor near the machine 10. Additionally, it will be understood that the calibration process would be performed before lines of the machine 10 are coupled to a patient.

The container 20 includes a bottom 21 and an upstanding sidewall 22 that defines a container 20 interior 23. In the illustrated embodiment, the container 20 includes an open top 24 such that the container 20 is open to the atmosphere. In this way, the calibration process is not affected by external pressures. According to the invention, the container 20 further includes a container inlet 25 and a container outlet 26 that present openings 27, 28 through the sidewall 22 to provide passage into and out of the interior 23 of the container 20, respectively. While the container inlet and outlet 25, 26 may be disposed in any position appropriate to the calibration function, in order to ensure that the container outlet 26 remains at or below a fluid line 29 within the container 20, at least the container outlet 26 is preferably disposed proximate to the bottom 21 of the container 20. In the illustrated embodiment, both the container inlet and outlet 25, 26 are disposed proximate to the bottom 21.

In order to couple the first and second hoses 17, 18 to the container inlet and outlet 25, 26, appropriate connectors 31, 32 may be provided. In the illustrated embodiment, the connectors 31, 32 includes fittings 33, 34 that extend through and is secured within openings 35, 36 in the sidewall 22 by nuts or bushings 37, 38. To ensure or minimize opportunity for leakage at the openings 35, 36, washers 39, 40 are provided about the fittings 33, 34 on either side of the container sidewall 22. The connectors 31, 32 may be of any appropriate design, however. For example, in an alternate embodiment, one or both of the connectors 31, 32 may be adhered, sonic welded, or otherwise secured to the container 20. It will be appreciated that the connectors 31, 32 may be the same for the container inlet and outlet 25, 26, or varied designs may be utilized.

In the illustrated embodiment, the connectors 31, 32 present male portions 41, 42 that mate with the female ends 43, 44 of the first and second hoses 17, 18. In a preferred embodiment, the connectors 31, 32 present standardized male fittings in the form of so-called Hansen connectors.

The first and second hoses 17, 18 each have first and second ends 45, 46, 47, 48. The first end 45 of the first hose 17 is fluidly coupled to the pump inlet 15, while the first end 46 of the second hose 18 is fluidly coupled to the pump outlet 16. During the calibration process, the second end 47 of the first hose 17 is removably, fluidly coupled to the container outlet 26, while the second end 48 of the second hose 18 is removably, fluidly coupled to the container inlet 25. Following the calibration process, the container 20 may be emptied and the first and second hoses 17, 18 returned to their working positions within the dialysis machine 10.

In order to facilitate the decoupling of the hoses 17, 18 prior to emptying the container 20, the container 20 may be provided with one or more valves 49 at the container inlet and outlet 25, 26. For example, the connectors 31, 32 may include respective valves 49 that may be manually operated or that are automatically moved to the closed position when the associated hoses 17, 18 are disconnected from the connectors 31, 32.

Figure 6:
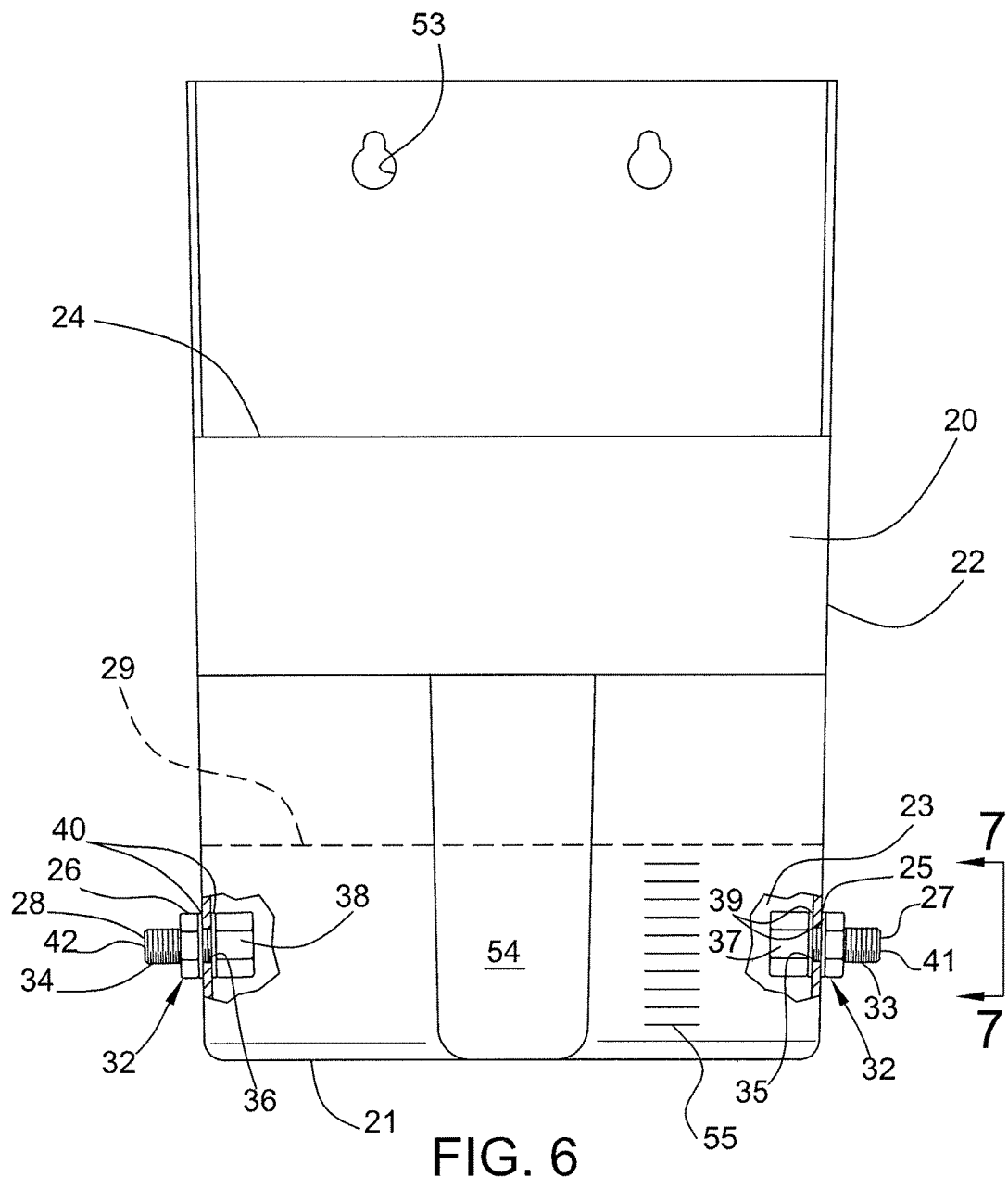
FIG. 6 is a front elevational view of the calibration fluid container of FIGS. 2-5 with portions broken away to show the connectors on either side of the container.
Figure 7:
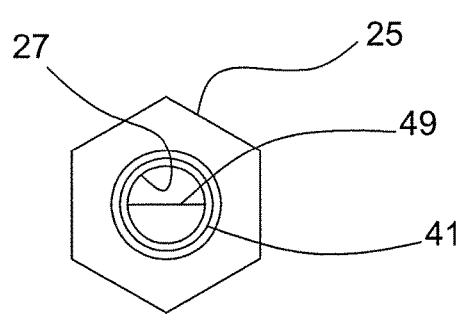
FIG. 7 is a side elevational view of a connector taken along line 7-7 in FIG. 6.

To further minimize the opportunity for spillage or upsetting the container 20, the dialysis machine 10 and container 20 may be provided with a coupling mechanism 50 whereby the container 20 may be temporarily coupled to the remainder of the dialysis machine 10. In the illustrated embodiment, hooks 51 in the form of button-like structures extend from an outer surface 52 of the housing 19 of the dialysis machine 10, while the container 20 includes corresponding keyhole-shaped mounting openings 53. As may be seen in FIGS. 2, 5 and 6, the mounting openings 53 may be disposed toward the top of the sidewall 22 in order to enhance stability when the container 20 is coupled to the remainder of the dialysis machine 10.

The container 20 and associated structures may be of any appropriate materials by any appropriate method. In an embodiment, the container 20 is injection molded of a polymer, such as, for example, polyethylene, or nylon. Alternate materials may include nonreactive metals, such as stainless steel. The container 20 may additionally include a handle 54 or the like to facilitate handling of the container 20. In the illustrated embodiment, the handle 54 is molded with the container 20, although it may alternately be later coupled to the container 20, and may be the same or a different material. The connectors 31, 32 may be formed of any appropriate materials such as, for example, PVC.

The container 20 may additionally include graduations 55 to provided the technician with an indication of the volume of fluid contained therein. Such graduations 55 may be provided to be visible on only the inside of the container 20, only the outside of the container 20, or both the inside and the outside of the container 20. Such graduations 55 may, for example, be molded into the container 20 or may be provided by a later applied scale. Typically, a relatively small amount of fluid is placed within the container 20 for calibration. In an embodiment, on the order of twenty-four cubic centimeters of fluid is utilized.

According to another aspect of the invention, a method for calibrating an ultrafiltration pump 14 in a dialysis machine 10 is provided. According to the method, a calibration fluid container 20 such as the container 20 described above is provided. As explained above, while the container 20 is illustrated mounted on the machine 10, it will be appreciated that calibration utilizing the container 20 may be performed with the container 20 at a higher or lower level, such as seated on the floor near the machine 10. According to such a method, the second end 47 of the first hose 17 is then removably, fluidly coupled to the container outlet 26, and the second end 48 of the second hose 18 is removably fluidly coupled to the container inlet 25. A calibration process is then performed on the ultrafiltration pump 14. Following calibration, the container 20 is emptied and the second ends 47, 48 of the first and second hose 18 are returned to their working positions within the dialysis machine 10. As discussed above the container 20 may be emptied either before or after the second ends 47, 48 of the first and second hoses 17, 18 are returned to their working positions. If one or more valves 49 are provided in the connectors 31, 32 of the container 20, the connectors 31, 32 may be disposed in appropriate positions to allow the passage of fluid when the hoses 17, 18 are coupled to the container 20, and to disallow the passage of fluid when the hoses 17, 18 are not coupled to the container 20.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

I claim:

1. A method for calibrating an ultrafiltration pump in a dialysis machine, the ultrafiltration pump having a pump inlet and a pump outlet, the ultrafiltration pump being adapted to pump fluid from the pump inlet to the pump outlet, the dialysis machine having first and second hoses, the first hose having first and second ends, the first end of the first hose being fluidly coupled to the pump inlet, a second hose having first and second ends, the first end of the second hose being fluidly coupled to the pump outlet, the method comprising the steps of:

providing a calibration fluid container, the container including a bottom, an upstanding sidewall, a container inlet and a container outlet, the bottom and the upstanding sidewall defining a container interior, the sidewall of the container including a plurality of graduations, the container defining an opening to the atmosphere, at least the container outlet being disposed in the sidewall proximate to the bottom, removably, fluidly coupling the second end of the first hose to the container outlet, and removably, fluidly coupling the second end of the second hose to the container inlet, performing a calibration process on the ultrafiltration pump, decoupling the second end of the first hose from the container outlet, and decoupling the second end of the second hose from the container inlet.

2. The method of claim 1 further comprising the steps of coupling the second end of the first hose to the machine, and coupling the second end of the second hose to the machine.

3. The method of claim 1 further comprising the step of emptying the container of fluid.

4. The method of claim/further including the step of placing fluid within the container.

5. The method of claim 1 further including the step of actuating at least one valve to provide flow between the pump and the container.

6. The method of claim 1 further including the step of coupling the container to the machine.

7. The method of claim 2 further including the steps of placing fluid within the container, coupling the container to the machine, actuating at least one valve to provide flow between the pump and the container, and emptying the container of fluid.

* * * * *